United States Patent [19]

Marshall

[11] Patent Number: 5,945,099

[45] Date of Patent: *Aug. 31, 1999

[54] MYCOHERBICIDAL DELIVERY COMPOSITIONS, PREPARATION AND METHODS FOR CONTROLLING AQUATIC WEEDS

[76] Inventor: Lucia G. I. Marshall, 5781 Summit Meadow Dr., St. Charles, Mo. 63304

[*] Notice: This patent is subject to a terminal disclaimer.

[21] Appl. No.: 09/072,298

[22] Filed: May 4, 1998

Related U.S. Application Data

[63] Continuation-in-part of application No. 08/721,609, Sep. 26, 1996.
[60] Provisional application No. 60/045,590, May 5, 1997.

[51] Int. Cl.⁶ .................................................. A01N 63/00
[52] U.S. Cl. .................. 424/93.1; 424/404; 424/489; 504/117; 504/150
[58] Field of Search .......................... 424/93.1, 93, 404, 424/489; 426/250, 148, 177; 504/117, 150; 514/75

[56] References Cited

U.S. PATENT DOCUMENTS

| | | | |
|---|---|---|---|
| 3,885,052 | 5/1975 | Starr | 426/250 |
| 4,036,228 | 7/1977 | Theeuwes | 165/69 |
| 4,097,261 | 6/1978 | Conway et al. | 504/117 |
| 4,560,527 | 12/1985 | Harke et al. | 264/500 |
| 4,716,039 | 12/1987 | Rogoff et al. | 424/93 |
| 4,983,389 | 1/1991 | Levy | 424/404 |
| 5,019,564 | 5/1991 | Lowe et al. | 514/75 |
| 5,023,080 | 6/1991 | Gupta | 424/405 |
| 5,055,300 | 10/1991 | Gupta | 424/409 |
| 5,079,005 | 1/1992 | Gupta | 424/408 |
| 5,210,184 | 5/1993 | Chajuss | 530/370 |
| 5,439,911 | 8/1995 | Ohtsuka et al. | 514/256 |

FOREIGN PATENT DOCUMENTS

| | | |
|---|---|---|
| 1 642 233 | 4/1971 | Germany . |
| 32 42 798 A1 | 11/1982 | Germany . |
| 195 09 936 | 3/1995 | Germany . |
| 2 242 130 | 9/1991 | United Kingdom . |
| WO 91/15117 | 3/1991 | WIPO . |
| WO 95/31101 | 11/1995 | WIPO . |

OTHER PUBLICATIONS

Shearer, J.F. (1996). "Field and laboratory studies of the fungus *Mycoleptodiscus terrestris* as a potential agent for management of the submersed aquatic macrophyte *Hydrilla verticillata*," Technical Report A–96–3, U.S. Army Engineer Waterways Experiment Station, Vicksburg, MS.

Shearer, J.F. (1996). "Potential of a pathogen, *Mycoleptodiscus terrestris*, as a biocontrol agent for the management of *Myriophyllium spicatum* in Lake Guntersville Reservoir," Technical Report A–96–4, U.S. Army Engineer Waterways Experiment Station, Vicksburg, MS.

Shearer, Judy F. (1997). "Endemic Pathogen Biocontrol Research on Submersed Macrophyts: Status Report 1996," Technical Report A–97–, U.S. Army Engineer Waterway Experiment Station, Vicksburg, MS.

Database WPI Section Ch, Week 9323 Derwent Publications Ltd., London, GB; Class B07, AN 93–185350 XP002052620 & JP 05 112 772 A (SANEI TOKA KK); May 7, 1993, abstract.

Patent Abstracts of Japan, vol. 11, No. 176 (C–426), Jun. 5, 1987 & JP 62 004209 A (Takeda Chem Ind), Jan. 10, 1987, abstract.

*Primary Examiner*—James Ketter
*Assistant Examiner*—Irem Yucel
*Attorney, Agent, or Firm*—Grace J. Fishel

[57] ABSTRACT

A mycoherbicidal delivery composition prepared from an inoculum of a fungal pathogen in an amount sufficient to control growth of an aquatic weed on a biocarrier comprising a plurality of discrete particles derived from a residual cell mass remaining fter lipids, proteins and sugars have been removed from oil seeds. The composition is formed as a cohesive, non-agglutinating dough which is shaped and dried to a low moisture content. The composition is shelf stable in dried form and can be used for targeted delivery of the mycoherbicide to an aquatic weed.

22 Claims, 1 Drawing Sheet

MYCOHERBICIDAL DELIVERY COMPOSITIONS, PREPARATION AND METHODS FOR CONTROLLING AQUATIC WEEDS

This application is a continuation-in-part of U.S. application Ser. No. 08/721,609, filed Sep. 26, 1996, for Biological Control Agent Biocarriers and Method of Formation and claims the benefit of U.S. provisional patent application Ser. No. 60/045,590, filed May 5, 1997, for Biopesticide Formulation.

BACKGROUND OF THE INVENTION

1. Field of the Invention

The present invention relates to mycoherbicidal delivery compositions, their preparation and to biological methods for controlling aquatic weeds.

2. Brief Description of the Prior Art

Infestations of aquatic weeds such as hydrilla result in an array of ecosystem disruptions by preventing sunlight from reaching other plants and animals. The plants can multiply in such numbers that they choke lakes and rivers, causing eutrophication. The vegetative mat can interfere with navigation, disrupt the functioning of drainage, irrigation, flood control and water conservation projects, block the withdrawal of water to hydroelectric and water plants, provide breeding grounds for disease carrying mosquitoes and snails, and reduce the fish population.

The most common methods for controlling the growth of nuisance aquatic weeds have been mechanical and chemical. A more environmentally friendly and cost-effective technique would make use of biological agents such as mycoherbicides.

Prior art formulations for controlling aquatic weeds such as hydrilla with *Mycoleptodiscus terrestris* have included product forms such as fermentation slurries, emulsifiable oils, syrups, cellulose, gums and alginates. For ease of application, granules or pellets are preferred. Prior art formulations of *M. terrestris* offer non-targeted control of aquatic weeds and other pests since the particle sizes, densities and intrinsic coacervating gelling properties of the formulations make the particles fall off the targeted surfaces. Previous formulations tend to dilute themselves in water or sink to the bottom thus diluting the biological control agent and missing the target plant. The formulations require higher application rates than would be required if the material could be applied in a more targeted fashion. In prior art granule and pellet formulations, the viability of the fungus is reduced, particularly when the fungus is present as mycelium.

Prior art formulations with wheat flour and other starches gel or agglutinize in the presence of moisture during processing in extruders, tablet presses and pelletizers and do not disperse well in water. Formulations with corn cob grit float and do not target submerged aquatic plants. Other nut shell grits such as almond and peanut hull grits similarly float and do not coat submerged aquatic plants.

Ideally, the viability of the fungus would be maintained and the granule or pellet would dissolve or break apart in such a manner that the fungus is suspended in the water near the weed in a form that it adheres to the plant, allowing sufficient contact time for infection. These objectives are critical to the practical success of a mycoherbicide for aquatic weeds, particularly those that are submerged, and have not been satisfied by prior art delivery compositions.

BRIEF SUMMARY OF THE INVENTION

In view of the above, it is an object of the present invention to provide a method for biocontrol of aquatic weeds, insects and other pests using a mycoherbicide in a biological carrier with or without additional chemical or biological pesticides or microbial environmental remediation agents. It is another object to provide a mycoherbicidal delivery composition that is shelf stable, can be provided as a dry product as a dust, granule, tablet, etc., preferably with 10–12% moisture, without adversely affecting the viability of the mycoherbicide. It is also an object to provide a method and mycoherbicidal delivery composition for targeted delivery of the mycoherbicide to the targeted weed by providing for dispersion of the mycoherbicide, floatation, wetting and submersion of the mycoherbicide in the vicinity of the target weed and coating the plant with the tackiness of the biocarrier to selectively deliver the mycoherbicide to the target weed. Other objects and features of the invention will be in part apparent and in part pointed out hereinafter.

In accordance with the invention, a mycoherbicidal delivery composition includes an inoculum of a fungal pathogen in an amount sufficient to control growth of a targeted aquatic weed. The inoculum is in a biocarrier comprising a plurality of discrete particles derived from a residual cell mass remaining after lipids, proteins and sugars have at least in part been removed from crushed or ground oil seeds. The mycoherbicidal delivery composition can be used for targeted control of an aquatic weed whose growth is controlled by the mycoherbicide.

The mycoherbicidal delivery composition is made by mixing an effective amount of an inoculum of the fungal pathogen in an amount sufficient to control growth of the targeted aquatic weed with a biocarrier as described above, with the inoculum containing enough water to prepare a non-agglutinating, cohesive dough. The dough is rolled out, extruded or otherwise shaped and dried to form a product having a low moisture content.

The invention summarized above comprises the compositions and methods hereinafter described, the scope of the invention being indicated by the subjoined claims.

DETAILED DESCRIPTION OF THE INVENTION

Figure 1:
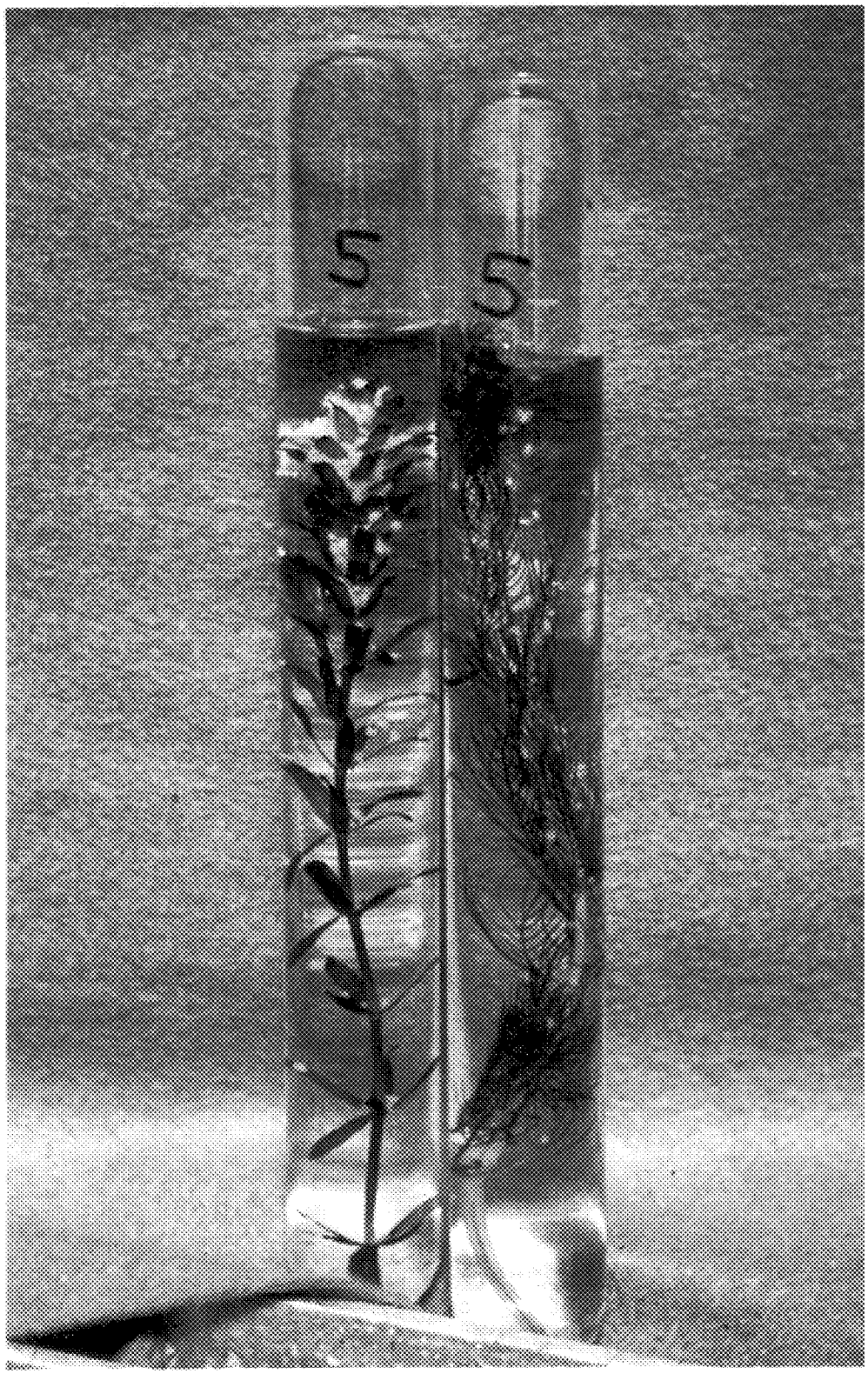
FIG. 1 shows a sprig of hydrilla in a test tube on the left and a sprig of Eurasian milfoil on the right treated with a mycoherbicidal delivery composition containing *M. terrestris* in accordance with the present invention. The figure demonstrates that the optimum particle size can be customized to the weed species to provide coating of the leaf surfaces.

In accordance with the present invention, a mycoherbicidal delivery composition is provided for controlling aquatic weeds. The term "aquatic weeds" includes plants that grow in an around aquatic bodies, including those that are submerged below water, float freely on top of the water or grow with foliage partly or entirely emergent from the surface. Waterhyacinth (*Eichhornia crassipes,* etc.) and hydrilla (*Hydrilla verticillata*) are common nonindigenous aquatic weeds. Other prohibited aquatic weeds (7 U.S.C. 2803 and 2809; 7 CFR 2.17, 2.51 and 371.2(c)) are *Alternanthera philoxeroides* (alligator weed), *Azolla pinnata* (azolla), Casuarina (all species) (Australian pine), *Crassula helmsii* (swamp stonecrop), *Hygrophila polysperma*

(hygro), *Iponoea aguatica* (water spinach), *Lagarosiphon* (all species) (African elodea), *Limnocharis flava* (Sawah-flowering rush), *Limnophila sessiliflora* (ambulia), *Lythrum salicaria* (purple loosestrife), *Melaleuca quinquenervia* (melalleuca), *Mimosa pigra* (catclaw mimosa), *Monochoria hastata, Monochoria vaginalis, Myriophyllum spicatum* (Eurasian watermilfoil), *Nechamandra alternifolia, Oryza rufipogon* (wild red rice), *Pontederia rotundifolia, Sagittaria sagittifolia,* Salvinia (all species except *S. rotundifolia*), *Schinus terebinthifolius* (Brazilian pepper-tree), *Sparganium erectum* (exotic bur-reed), *Stratiotes aloides* (water soldier), Trapp (all species) (water-chestnut (not Chinese water chestnut)) and *Vossia cuspidata* (hippo grass).

Endemic fungal pathogens are isolated from diseased plant material by plating it onto an agar media selective for fungal pathogens. The candidate fungi are then screened for effectiveness as a mycoherbicide. The following fungi have been identified as pathogens of hydrilla: *M. terrestris*, Rhizopus species, Aspergillus species, Trichoderma species, Rhizoctonia species, *Fusarium roseum* and *Fusarium Culorum*. Fungal pathogens for waterhyacinth include *Cercospora piaropi* and *Cercospora rodmanii* and fungal pathogens for Eurasian milfoil include *M. terrestris, Fusarium sporotricoides, Acremonium curvulum,* Pythium species, *Curvularia inaequalis, Cylindrocarpon lucidum,* Cylindrocarpon destructans, Macrophoma species, Trichoderma species, Phomopsis species, *Sclerotium roflsii,* Paecilomyces species, *Colletotrichum gloeosporioides, Aspergillus fumigatuus,* Polyscytalum species and Moniliaceous species.

It will be understood that the above lists of aquatic weeds and fungal pathogens for control of them is representative and not intended to be limiting. Other members of both lists can and will be added by those skilled in the art. Preferably, the mycoherbicides will be indigenous to the particular weed being controlled, thereby allaying the natural fears associated with the use and release of microbials into the environment.

For use in the mycoherbicidal delivery compositions of the present invention, a fungal pathogen of a target aquatic weed is grown in a suitable aqueous culture medium for sufficient time to produce adequate fungal biomass. Any culture medium in which the desired microorganisms will effectively grow can be used. Agents to suppress sporulation and antibiotic compounds to ensure biological purity of the fungal culture during the production process may be added.

The culture medium may be inoculated with an inoculum stock (i.e., seed culture) which is produced by plating the selected fungal pathogen on SYE (sucrose-yeast extract agar) or PDA (potato dextrose agar), excising plugs from the culture which may contain mycelium or mycelium plus spores, and homogenizing the plugs with culture medium. This type of inoculum stock, i.e., mycelium stock or mycelium plus spores stock, should be used immediately after preparation.

The culture medium is inoculated with the inoculum stock in a fermenter to produce a biomass which is preferably primarily mycelial. If more biomass is desired, then this culture can be serially-transferred to one or more larger fermenters. After sufficient mycelial biomass has been generated, the fungal slurry is then homogenized for sufficient time to uniformly mix the propagules and incorporated into a biocarrier more particularly described below.

The fermentation is preferably performed under controlled conditions for temperature, pH, aeration, agitation, backpressure and dissolved oxygen, in order to optimize the production of the mycelial biomass. For culture volumes of *M. terrestris* grown in 1 l shake flasks on modified Richard's V-8 juice broth as described in Example 1, the conditions used for temperature are between about 20 and 29° C., pH between about 6.2 and 8.5, and agitation between 180 and 275 rpm. The time period for completion of fermentation will range between about 4 and 7 days, depending on the time needed to generate the required volume of mycelial biomass required. The fungal slurry is then homogenized in a commercial blender for the purpose of cutting up the fungal biomass into the largest number of units that are still viable and used as the source of pathogenic fungus in formulations for controlling aquatic weeds in accordance with the present invention.

The biocarriers used in the present invention are a by-product of oil seed processing. When oil seeds such as soybeans, corn, oats, sesame, peanuts, canola, rape seed, cotton seed, wheat, barley, alfalfa, rice, rye and so forth are crushed or ground and subjected to physical and chemical extraction processes to separate the edible from the inedible or undesirable parts not ordinarily used for food, there remains a by-product waste stream having little or no economic value. This by-product comprises a residual cell mass including cell walls, membranes and microfilaments, which in the case of soybeans is primarily the carbohydrate portion of the soybean cotyledon.

When the biocarrier is produced from soybeans, for example, the soybeans are crushed or ground in a conventional fashion, and passed through a conventional oil expeller. The oil is preferably removed by solvent extraction, using solvents normally employed for this purpose. The resulting solids, commonly referred to as high DPI soybean flakes, contain many ingredients including complex proteins, sugars, fibers and others. The proteins and sugars are dissolved out of the solids. This may be done by adding the flakes to an aqueous bath and adding a food grade alkaline material to raise the pH substantially above 7. Typical of such alkaline reagents are sodium hydroxide, potassium hydroxide, calcium hydroxide or other commonly accepted food grade alkaline reagents. The material is than extracted for a period of time sufficient to put the proteins and sugars in solution, usually about 30 minutes or so. The resulting liquor solution is separated from the solids, as by passing the material through a screen and/or centrifuging. The solids, the residual cell mass, is dried and then milled to a suitable size, e.g. between about 20 to about 200 microns, using a hammer mill followed by air-milling to obtain a suitable particle size distribution for use as described below.

A commercially available source of soybean residual cell mass is sold by Protein Technologies International under the trademark POLY-SOY. The composition of POLY-SOY is given below:

| ASSAY | LEVEL (% by weight) |
|---|---|
| Moisture | 10.0 |
| Protein (As is) | 12.0 |
| Protein (Dry basis) | 13.3 |
| Fat | 1.0 |
| Ash | 4.0 |
| Carbohydrate | 73.0 |
| Calcium 1.0 | |
| Phosphorus | 0.5 |
| Magnesium | 0.2 |
| Potassium | 0.95 |
| Sodium | 0.2 |
| Iron | 110 ppm |

-continued

| ASSAY | LEVEL (% by weight) |
|---|---|
| Manganese | 21 ppm |
| Zinc | 24 ppm |
| Copper | 2 ppm |

An effective amount of fungal biomass, preferably as a homogenate, is mixed with the biocarrier to form a cohesive and homogeneous, non-agglutinating, dough. An effective amount is defined as that quantity of fungal ingredient which will achieve the desired level of weed control in use. Usually a biocarrier to slurry ratio (by weight) of 1:3 is optimum, depending on the effects of other ingredients which may be included as more particularly discussed below. The dough is rolled out into a sheet or extruded or formed into special shapes such as thin strips or into pasta-like configurations familiar to the food industry. The strips or configurations may be cut into lengths forming granules. The rolled or extruded dough is dried at temperatures that are safe for the fungi biomass, typically below 35° C., and preferably at 15–30° C. until the composition has a water content of about 8–15%, preferably about 10–12%. The dried sheet of dough can be broken up or ground into granules or dust. The granules may be sieved to obtain the size range desired and then compressed into tablets. The dried product can also be incorporated in a liquid, paste or jelly-like medium, or is admixed with an inert solid granular or particulate carrier. For application, for example, to the foliage of aquatic plants above water, formulations in the form of wettable powders and aqueous suspensions designed to be diluted with water before spraying may be preferred. These compositions may also incorporate conventional emulsifying agents, suspending agents and the like. In whatever dried form (dust, granules, tablets, etc.), the mycoherbicidal delivery compositions of the present invention are shelf stable for commercially acceptable periods of time under ambient conditions or refrigeration.

The addition of materials to the mycoherbicidal delivery compositions to alter the density of the final products is also contemplated, such as high density materials that would cause the products to sink and low density materials that would cause the products to float. A combination of two or more compatible weed pathogenic fungi, or a fungal pathogen combined with other compatible biological control agents, may be included, where feasible, to broaden the pesticidal properties of the products of this invention. Adjuvants, or other additive ingredients, may also be included.

The term "biological control agents" includes agrochemicals, biopesticides, environmental remediation enhancers or mixtures thereof. Included within the term "agrochemicals" are herbicides, fungicides, bactericides, acaricides, insecticides, gametocides, nematocides, algicides, rodenticides, molluscides, insect baits, repellents, pheromones, insect growth regulators, fertilizers, micronutrients, soil conditioners, growth regulators and the like, or mixtures thereof. It should also be understood that the term "agrochemical" includes agricultural, horticultural, fruticultural and floricultural use. The term "biopesticides" includes fungi, viruses, bacteria, toxins and the like, as well as mixtures thereof, including mixtures of biopesticides with agrochemicals. The biocarrier contains micronutrients that may be useful to the soil during crop treatment and may provide micronutrients to nurture any biopesticide during storage and application. The term "environmental remediation enhancer" includes bacteria that degrade petroleum hydrocarbons and the like.

Granules, tablets or other product configurations produced in accordance with the present invention may be applied post emergence to an environment with aquatic weeds. The biocarriers provide the matrix structure for the mycoherbicidal delivery compositions of the present invention and may also serve as a nutrient source that may be beneficial to some types of fungi that are carried therein. When an effective amount of the granules or tablets are applied to the aquatic weeds, the fungal pathogen will infect the target weed, thereby controlling its growth or killing it. An effective amount is that quantity of product which will result in a significant level of weed damage as compared to an untreated group. The actual amount may vary with the particular weed pathogen, the maturity and susceptibility of the target weed, and various environmental conditions. As the granule or tablet slowly dissolves, the fungus is suspended in the water near the weed in such a form that it adheres to the plant, allowing sufficient contact time for infection. Hence, the granules or tablets provide targeted delivery of the mycoherbicide to the aquatic weed to be controlled due to the dispersion of the delivery composition in the vicinity of the weed and the coating and tackiness of the biocarrier that selectively delivers the pathogenic fungus to the targeted aquatic weed.

When the target weed is hydrilla and the fungal pathogen is *M. terrestris*, better control is realized when the mycoherbicidal delivery composition is applied early in the growing season, perhaps because the young plants are more susceptible to ingress of *M. terrestris*. Temperature may also be a factor in disease development as the optimum temperature for fungal growth is between 22 and 28° C. Cooler temperatures earlier in the growing season may be more favorable to fungal growth than are elevated temperatures later in the season. The application rate should be in the range of about 200 cfu (colony forming units)/cm$^2$ of target area. Preferably, the application rate should be in the range of about 100 to 2,000 cfu/cm$^2$. Application rates less than 100 cfu/cm$^2$ are primarily useful in a formulation including a second herbicide.

The attack of the mycoherbicide on hydrilla is manifested by chlorosis of the leaf tissue, a complete loss of leaf color in about 7 days and plant disintegration within about 10 days. Studies have confirmed that the fungus is effective because it destroys the cellular integrity of plant tissues, resulting in collapse of the entire plant.

The following examples illustrate the invention.

EXAMPLE 1

Seed cultures were prepared by plating *M. terrestris* onto potato dextrose agar plates (PDA) (Difco Laboratories, Detroit, Mich.). The cultures were incubated in the dark at 28° C. for seven days. Plugs 4 mm in diameter were cut from the leading edge of the fungal colony. Five plugs of fungal mycelium were added to 1 l Erlenmeyer flasks, each containing 500 ml of modified Richard's V-8 juice broth (glucose, 10 g; $KNO_3$, 10 g; $CaCO_3$, 3 g; V-8 juice (Campbells), 200 ml; $H_2O$, 800 ml). The flasks were placed on a platform shaker (New Brunswick, Edison, N.J.) and agitated at 200 rpms. After six days, the mycelial mat was filtered through four layers of cheesecloth, suspended in 100 ml of sterile water, and comminuted in a blender for 80 sec. Dilutions of the fungal suspensions were plated onto Martin's agar ($H_2O$, 1 l; agar, 17 g; $KH_2PO_4$, 0.5 g; $K_2HPO_4$, 0.5 g; $MgSO_4$.7 $H_2O$, 0.5 g; peptone, 0.5 g; dextrose, 10 g; yeast extract, 0.5 g; rose bengal, 0.05 g; streptomycin sulfate, 0.03 g) to determine propagule density. The above procedures consistently result in a slurry with a colony forming unit count (cfu) of $1\times10^6$ colony forming units (cfu)/ml. The fungal colony was stored overnight in an ice-cooled chest for processing into granules as described in the following example.

EXAMPLE 2

Four liters of the fungal slurry prepared in Example 1 was added to 1360 g soybean residual cell mass sold by Protein Technologies International under the trademark POLY-SOY in a stainless steel mixing vessel. The slurry and the soybean residual cell mass were mixed together at 25° C. to form a wet non-agglutinating, dough mixture.

A portion of the dough mixture was extruded in a pasta extruder, Pasta Express, Model X3000 (Creative Technologies, Inc., Brooklyn, N.Y.) through a circular die. The extrudate had a diameter of 1 mm and was cut into pellets measuring 5 mm long. The pellets were spread a single layer thick on aluminum trays and dried under forced air at 25° C. to a moisture content of 10% by weight.

Another portion of the dough mixture was spread onto aluminum trays and dried as described above to a moisture content of 10% by weight. The dried dough was then broken into particles, 10 to 40 mesh in size, and tablets, having a nominal diameter of 0.6 cm and a length of 1.7 cm, were formed in a Colton Model 330, 2-ton press.

The number of cfu/g of *M. terrestris* formulated on the carrier was determined by suspending a 0.5 g subsample of dry granules and tablets in 10 ml of sterile water and plating a series of dilutions on Martin's agar. After four days incubation at room temperature, *M. terrestris* colony counts were determined by visual examination of the plates. The number of cfu/g in the granules and tablets was consistently $1\times10^5$ cfu/g. Samples of the granules were kept cool and plated weekly on Martin's agar to access viability. Viability was confirmed through consistent fungal retrieval up to three months following production of them, at which time the supply of granules was depleted.

EXAMPLE 3

The efficacy of the granules and tablets from Example 2 at infecting hydrilla were tested in test tube studies reported by Shearer (Shearer, J. F. 1998. Biological control of hydrilla using an endemic fungal pathogen. J. Aquat. Plant Manage. 36), as follows:

Sprigs of hydrilla 15 cm in length were collected from greenhouse hydrilla stock cultures, thoroughly washed in tap water, and placed in test tubes containing 60 ml of sterile water. An approximate 1 g dose (800 cfu/ml) of granules or one tablet of the formulated fungus was added to the water and allowed to dissipate over the plant material. Treatments were replicated five times. The test tube cultures were placed in a 26° C. incubator set to a 12/12 light/dark cycle. After two weeks the plants were visually examined and rated for disease damage(0=no damage; 1=slight leaf chlorosis, 2=general chlorosis of leaves and stems; 3=leaves and stems chlorotic and flaccid; 4=total plant collapse). Subsamples of the granules and tablets were kept cool and plated weekly onto Martin's agar to assess fungal viability. At two weeks post inoculation, damage on hydrilla using granules or tablets was assessed a disease rating between 3 and 4 (i.e., the hydrilla sprigs were severely chlorotic and flaccid or collapsed in the bottom of the tube).

EXAMPLE 4

The effectiveness of the granules prepared in Example 2 was compared with the effectiveness of the slurry prepared in Example 1 at controlling the growth of hydrilla in columns was as follows (Shearer 1998):

Clear acrylic columns (76 cm tall by 13.7 cm wide) (12 l) were used for small-scale greenhouse testing. Thirty-two-ounce plastic cups filled three-fourths full with lake sediment amended with ammonium chloride (0.5 g/l) and Esmigran (1.75 g/l) were overlain with five cm of tap-water-washed silica sand. Three 15-cm apical springs of hydrilla were planted in the sediment and the cups placed in the bottom of the column. Twelve liters of nutrient solution (Smart and Barko 1985) were added to each column. The columns were aerated and maintained at 25±1° C. in an environmental chamber (Conviron, Pembina, N.D.). Plants were allowed to grow approximately four weeks before testing was initiated. Five, 10, and 20 g of formulated fungus were applied to the surface of the water. Allowing for dilution, in the 12 l columns, the effective rates were approximately 42, 83 and 167 cfu/ml, respectively. Low- and medium-dose treatments of the fungal slurry were applied at rates of 5 and 10 ml (400 and 800 cfu/ml), respectively. Each treatment was replicated three times. After four weeks, three stem pieces 2 cm in length were collected from plants or floating plant tissue in each column, surface sterilized in a 10% bleach solution (0.5% NaOCl) for 1 min, rinsed in sterile water, and plated onto Martin's agar to determined presence/absence of the fungus in the plant tissue. The remainder of the aboveground biomass from each column was harvested and dried to a constant weight at 60° C. The results are reported in Table I below.

TABLE I

| Treatment | Control | Slurry (5 ml) | Slurry (10 ml) | Granules (5 g) | Granules (10 g) | Granules (20 g) |
|---|---|---|---|---|---|---|
| Dry weight (g) | 13.91 | 1.91 | 0.76 | 1.71 | 0.73 | 0.1 |
| Percent reduction | — | 86.3 | 94.5 | 87.7 | 94.8 | 99.2 |

As shown in Table I, the fungal slurry of *M. terrestris* rated at $1\times10^6$ cfu/ml applied at 5 ml and 10 ml to rooted hydrilla reduced shoot tissue 86.3 and 94.5%, respectively, by four weeks post inoculation. Comparable reductions in hydrilla shoot biomass, 87.7 and 94.8%, were achieved with applications of 5 g and 10 g, respectively, of *M. terrestris* rated at $1\times10^5$ cfu/g. At the highest rate of application (20 g), the formulation reduced biomass by 99.2%.

EXAMPLE 5

The granules from Example 2 were tested for control of hydrilla growing in tanks outdoors as follows (Shearer 1998):

Tanks (160 cm in diameter by 92 cm deep, approximately 1700 l) were used for testing. Lake sediment was amended as described in Example 4 above. Plastic containers (36 cm by 30 cm by 13 cm) were filled with sediment to a depth of 8 cm and overlain with 4 cm of tap-water-washed silica sand. Twenty-five apical springs of hydrilla 15 cm in length were planted in each container. Ten containers were placed in each of six tanks and the tanks filled with nutrient solution (Smart and Barko 1985). The plants were allowed to grow until they reached the water surface and formed a canopy. The granular formulation was dispersed in 400-g does over the water surface of treated tanks and allowed to naturally dissipate onto hydrilla tissue. The effective application rate allowing for dilution was 23 cfu/ml. Treatments were replicated three times. After four weeks, aboveground biomass was harvested from treated and control tanks. Small subsamples of plant stem tissue, 2 cm in length, were taken from each sample to assay for presence/absence of the fungal components. The remaining biomass was dried to a constant weight at 60° C. The results as shown in Table II.

By week one of the tank study, disease symptoms were apparent on hydrilla. Leaves were chlorotic and there was evidence of the fragmentation. By week three of the study, the epidemic had waned and little hydrilla tissue remained in the treated tanks. Because the tanks were outdoors, there was some concern that insects might transmit fungal inoculum to untreated hydrilla, but at the four-week-post inoculation harvest, *M. terrestris* was not recovered from hydrilla shoot tissue collected from treated or control tanks.

TABLE II

| Treatment | Control | Granules |
|---|---|---|
| Dry weight (g) | 391.2 | 9.66 |
| Percent reduction | — | 97.5 |

As shown in Table II, four weeks post inoculation, hydrilla shoot biomass was reduced 97.5% compared to untreated controls. The effective rate of fungal inoculum used in each tank (24 cfu/ml) was 65% lower than the effective rate of the low dose treatment of the column study (42 cfu/ml). In previous tank studies, inoculum applied in the form of a fungal slurry reduced hydrilla shoot biomass by 85% (Shearer, J. F. 1994. The use of pathogens for the management of hydrilla and Eurasian watermilfoil. Proceedings, 29th Ann. Meeting, Aquatic Plant Control Research Program, MP A-95-3, US Army Engineer Waterways Experiment Station, Vicksburg, Miss. pp. 124–129.)

EXAMPLE 6

A tablet formula can be prepared as described above to treat surface aquatic plants and submerged aquatic plants comprising:

| Percent by weight | Ingredient |
|---|---|
| 10 | *M. terrestris* slurry |
| 8 | Glyphosidic acid; glyphosate salt; or derivative of glyphosate |
| 8 | Sodium bicarbonate |
| 74 | Residual soybean cell mass |

EXAMPLE 7

A granular formula can be prepared as described above to treat aquatic plants comprising:

| Percent by weight | Ingredient |
|---|---|
| 10 | *M. terrestris* slurry |
| 5 | Fluridone |
| 85 | Residual soybean cell mass |

EXAMPLE 8

A granular formula can be prepared as described above to treat aquatic plants comprising:

| Percent by weight | Ingredient |
|---|---|
| 10 | *M. terrestris* slurry |
| 5 | Mecoprop (2-4D) |
| 85 | Residual soybean cell mass |

EXAMPLE 9

A granular formula can be prepared as described above containing both a mycoherbicide and a bacterial insecticide:

| Percent by weight | Ingredient |
|---|---|
| 10 | *M. terrestris* slurry |
| 10 | *Bacillus sphaericus* slurry |
| 80 | Residual soybean cell mass |

EXAMPLE 10

A granular formula can be prepared as described above containing both a mycoherbicide and a mycoinsecticide:

| Percent by weight | Ingredient |
|---|---|
| 10 | *M. terrestris* slurry |
| 10 | *Lagenidium giganteum* slurry |
| 80 | Residual soybean cell mass |

In view of the above, it will be seen that the several objects of the invention are achieved and other advantageous results attained. As various changes could be made in the above compositions and methods without departing from the scope of the invention, is intended that all matter contained in the above description or shown in the accompanying drawings shall be interpreted as illustrative and not in a limiting sense.

What is claimed:

1. A mycoherbicidal delivery composition comprising an inoculum of a fungal pathogen in an amount sufficient to control growth of an aquatic weed in a biocarrier comprising a plurality of discrete particles obtained from a residual cell mass remaining after lipids, proteins and sugars have at least in part been removed from crushed or ground oil seeds.

2. The composition of claim 1 wherein the inoculum is mycelium or mycelium and spores, said composition having a moisture content between 8 and 15% by weight water.

3. The composition of claim 1 wherein the aquatic weed is *Hydrilla verticillata,* Eichhornia, *Alternanthera philoxeroides,* Azolla, Casuarina, *Crassula helmsii, Hygrophila polysperma, Iponoea aquatica,* Lagarosiphon, *Limnocharis flava, Limnophila sessiliflora, Lythrum salicaria, Melaleuca quinquenervia, Mimosa pigra, Monochoria hastata, Monochoria vaginalis, Myriophyllum spicatum, Nechamandra alternifolia, Oryza rufipogon, Pontederia rotundifolia, Sagittaria sagittifolia,* Salvinia (except *S. rotundifolia*), *Schinus terebinthifolius, Sparganium erectum, Stratiotes aloides,* Trapp or *Vossia cuspidata.*

4. The composition of claim 1 wherein the particles and the inoculum of a fungal pathogen are mixed with an agrochemical, a biopesticide, an environmental remediation enhancer or a mixture thereof.

5. The composition of claim 4 wherein the agrochemical is a herbicide, fungicide, bactericide, acaricide, insecticide, gametocide, nematocide, algicide, rodenticide, molluscide, insect bait, repellent, pheromone, insect growth regulator, fertilizer, micronutrient, soil conditioner, growth regulator or mixture thereof.

6. The composition of claim 4 wherein the biopesticide is a fungus, virus, bacterium, toxin or a mixture thereof.

7. A mycoberbicidal delivery composition comprising a mycelium or mycelium and spores inoculum of a *Mycoleptodiscus terrestris* in an amount sufficient to control growth of an aquatic weed in a biocarrier comprising a plurality of discrete particles obtained from a residual cell mass remaining after lipids, proteins and sugars have at least in part been removed from crushed or ground oil seeds, said composition having a moisture content between 8 and 15% by weight water.

8. The composition of claim 7 in the form of dust, granules or pellets.

9. The composition of claim 8 and wherein the oil seeds are soybeans.

10. The composition of claim 9 wherein the particles and the inoculum of a *Mycoleptodiscus terrestris* are mixed with an agrochemical, a biopesticide, an environmental remediation enhancer or a mixture thereof.

11. The composition of claim 10 wherein the agrochemical is a herbicide, fungicide, bactericide, acaricide, insecticide, gametocide, nematocide, algicide, rodenticide, molluscide, insect bait, repellent, pheromone, insect growth regulator, fertilizer, micronutrient, soil conditioner, growth regulator or mixture thereof.

12. The composition of claim 10 wherein the biopesticide is a fungus, virus, bacterium, toxin or a mixture thereof.

13. A method of controlling the growth of an aquatic weed, comprising the step of applying a mycoherbicidal delivery composition to an area of aquatic weed with a mycoherbicidal delivery composition comprising an inoculum of a fungal pathogen in an amount sufficient to control growth of an aquatic weed in a biocarrier comprising a plurality of discrete particles obtained from a residual cell mass remaining after lipids, proteins and sugars have at least in part been removed from crushed or ground oil seeds.

14. The method of claim 13 wherein the composition has a water content between about 8 and 15% by weight and the inoculum is mycelium or mycelium and spores.

15. The method of claim 14 wherein the composition is a dust formulated in a liquid carrier, granules or tablets and is applied post-emergence of the aquatic weed.

16. The method of claim 15 wherein the aquatic weed is *Hydrilla verticillata,* Eichhornia, *Alternanthera philoxeroides,* Azolla, Casuarina, *Crassula helmsii, Hygrophila polysperma, Iponoea aquatica,* Lagarosiphon, *Limnocharis flava, Limnophila sessiliflora, Lythrum salicaria, Melaleuca quinquenervia, Mimosa pigra, Monochoria hastata, Monochoria vaginalis, Myriophyllum spicatum, Nechamandra alternifolia, Oryza rufipogon, Pontederia rotundifolia, Sagittaria sagittifolia,* Salvinia (except *S. rotundifolia*), *Schinus terebinthifolius, Sparganium erectum, Stratiotes aloides,* Trapp or *Vossia cuspidata.*

17. The method of claim 15 wherein the aquatic weed is *Hydrilla verticillata* and the oil seeds are soybeans.

18. The method of claim 14 wherein the particles and the inoculum of a fungal pathogen are mixed with an agrochemical, a biopesticide or a mixture thereof.

19. The method of claim 18 wherein the agrochemical is a herbicide, fungicide, bactericide, acaricide, insecticide, gametocide, nematocide, algicide, rodenticide, molluscide, insect bait, repellent, pheromone, insect growth regulator, fertilizer, micronutrient, soil conditioner, growth regulator or mixture thereof.

20. The composition of claim 18 wherein the biopesticide is a fungus, virus, bacterium, toxin or a mixture thereof.

21. A method for preparing a mycoherbicidal delivery composition comprising the steps:

(a) mixing an effective amount of an inoculum of a fungal pathogen in an amount sufficient to control growth of an aquatic weed with a biocarrier comprising a plurality of discrete particles obtained from a residual cell mass remaining after lipids, proteins and sugars have at least in part been removed from crushed or ground oil seeds, said inoculum containing enough water to prepare a non-agglutinating, cohesive dough;

(b) rolling out, extruding, or shaping said dough;

(c) drying said dough to form dust, granules or pellets.

22. The method of claim 21 wherein the inoculum is mycelium or mycelium and spores of *Mycoleptodiscus terrestris,* the oil seeds are soybeans and the composition is dried to a moisture content between 8 and 15% water.

* * * * *